United States Patent [19]

Link et al.

[11] 4,367,751

[45] Jan. 11, 1983

[54] APPARATUS AND PROCESS FOR PRODUCING ARTIFACT EFFECT ON SPHYGMOMETRIC INFORMATION

[75] Inventors: William T. Link, Berkeley; Jerry D. Haney, Sunnyvale; William Jansen, Palo Alto, all of Calif.

[73] Assignee: Warner-Lambert Company, Morris Plains, N.J.

[21] Appl. No.: 754,388

[22] Filed: Dec. 27, 1976

[51] Int. Cl.³ .............................................. A61B 5/02
[52] U.S. Cl. ..................................... 128/682; 128/681
[58] Field of Search ................... 128/2.05 A, 2.05 C, 128/2.05 D, 2.05 E, 2.05 G, 2.05 M, 2.05 Z, 2.05 Q, 680–683

[56] References Cited

U.S. PATENT DOCUMENTS

| | | | |
|---|---|---|---|
| 2,827,040 | 3/1958 | Gilford | 128/2.05 A |
| 3,552,383 | 1/1971 | Krueger et al. | 128/2.05 A |
| 3,581,734 | 6/1971 | Croslin et al. | 128/2.05 M |
| 3,903,872 | 9/1975 | Link | 128/2.05 A |
| 3,905,354 | 9/1975 | Lichowsky | 128/2.05 M |
| 3,985,123 | 10/1976 | Herzlinger et al. | 128/2.05 V X |
| 4,009,709 | 3/1977 | Link et al. | 128/2.05 M X |
| 4,027,662 | 6/1977 | Lee | 128/2.05 |
| 4,033,336 | 7/1977 | Murawski et al. | 128/2.05 A |

FOREIGN PATENT DOCUMENTS 1259502  1/1968  Fed. Rep. of Germany ... 128/2.05 M

OTHER PUBLICATIONS

Randall, M. J. et al., "Computer Automation of Blood Pressure Measurements", IEEE Proc. V. 63 #10, Oct. 1975, pp. 1399–1403.
"Semis Invade Medical Transducers, uPs Monitor EKG and Blood Pressure," Electronics Design, No. 19, Sep. 13, 1976, p. 28.

Primary Examiner—Kyle L. Howell
Assistant Examiner—Francis J. Jaworski
Attorney, Agent, or Firm—Louis S. Gillow

[57] ABSTRACT

Improved method and apparatus for indicating blood pressure and the like in a varied pressure cuff system wherein blood vessel pulsation signals are supplied to signal processing means for determining the blood pressure. The blood pressure pulsations are monitored to detect artifacts and the signal processing means inhibited if an artifact is detected. Upon detection of an artifact the pressure applied by the cuff is automatically adjusted to repeat the pressure at which the artifact is detected, thereby to seek artifact-free values. The pressure-repetition may be a discrete pressure or a limited pressure range. Further, a maximum number of limited-pressure repetitions may be established, after which the entire pressure range must be repeated.

14 Claims, 14 Drawing Figures

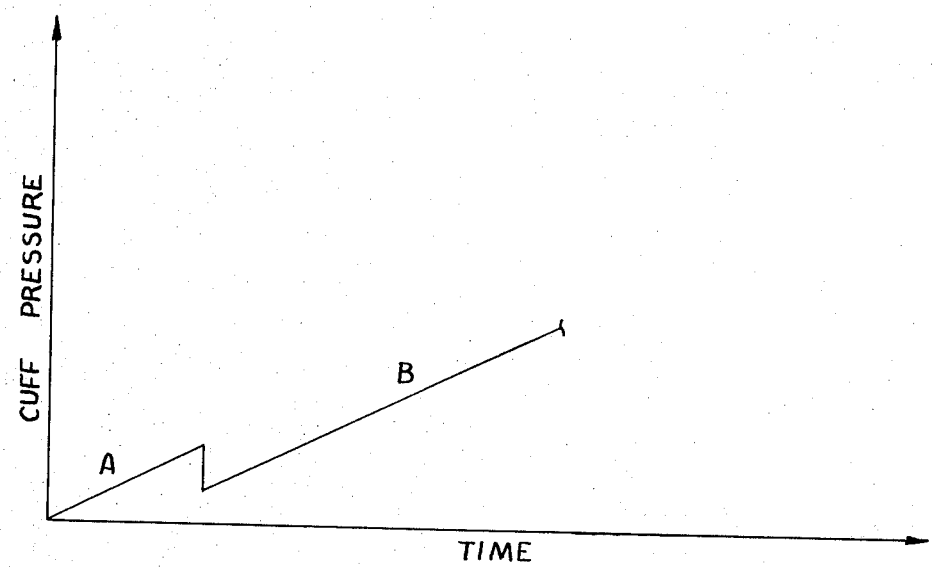
Fig. 4
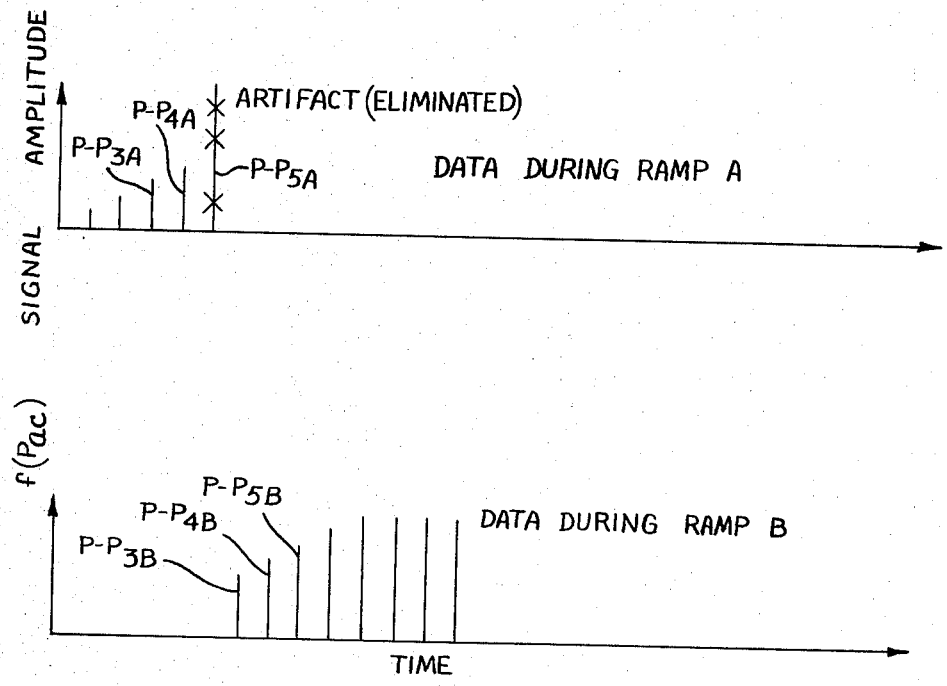
Fig. 5a
Fig. 5b

APPARATUS AND PROCESS FOR PRODUCING ARTIFACT EFFECT ON SPHYGMOMETRIC INFORMATION

BACKGROUND OF THE INVENTION

The present invention relates generally to apparatus and process for producing information indicative of the physical condition of the living test subject, and more particularly relates to improved apparatus and method for measuring a patient's blood pressure. More particularly still, the invention relates to an apparatus and a method for reducing the effects of signal artifact on blood pressure measurements.

The prior art is replete with devices for measuring the blood pressure of a living test subject. Basic to many of these devices and techniques is the inclusion of a pressure applying cuff which, through selective control of the applied pressure, operates to increasingly or decreasingly occlude a blood vessel embraced there within. Various forms of transducers are then employed for sensing phenomena of the blood vessel and/or the blood flow therein as a function of the pressure applied by the cuff. For example, in one well known technique a stethoscope is used to listen to Korotkoff sounds. More complicated methods and apparatus based on the same principle of listening to the Korotkoff sounds replace the mercury manometer with a mechanical or electromechanical pressure gauge and utilize microphone detection of the Korotkoff sounds which are analyzed electrically. In yet another technique, that of oscillometry, the transducer provides a signal having a waveform which pulsates and is in some way proportional to the magnitude and timing of the blood pressure within the blood vessel as a function of the pressure applied by the cuff.

Examples of these latter mentioned oscillometric techniques are found in U.S. Pat. No. 3,903,872 issued Sept. 9, 1975 to William T. Link for Apparatus and Process for Producing Sphygmometric Information, and in the U.S. patent application Ser. No. 578,047, filed May 15, 1975 by Link et al for Apparatus and Process for Determining Systolic Pressure, now U.S. Pat. No. 4,009,709 issued Mar. 1, 1977, both of which are incorporated herein by reference. In the blood pressure measuring techniques of the aforementioned U.S. Patents, a pressure transducer associated with the cuff operates to sense both the pressure applied by the cuff and a small pulsating signal component representative of the pulsations of a blood vessel embraced therein. Employing algorithms described in greater detail in the aforementioned patent and patent application, the signal provided by the cuff transducer, and more particularly the pulsating component thereof, is analyzed and processed by certain control and logic circuitry to obtain indications of the patient's diastolic and systolic blood pressures.

Basic to the accurate determination of blood pressures using the aforementioned and other techniques is the assumption that the signals received from the cuff and subsequently processed are representative substantially only of phenomena associated with the blood pressure within the blood vessel. However, the signal provided by the cuff transducer may occasionally include components whose amplitude and/or frequency constituents are non-representative of the pressure within the blood vessel. These signal components are generally termed artifacts and will be referred to herein as such. These artifacts may arise for a variety of reasons including voluntary and/or involuntary muscle activity on the part of the patient, pressure-related noise occurring in the general environment in which the blood pressure measurements are being taken, bumping and/or jiggling of the air conduits associated with the cuff, etc. In any event, these artifacts may comprise part of the signal received and analytically processed by the particular system and unless identified and someway compensated for, will distort or invalidate the blood pressure measurements ultimately obtained.

For the foregoing reasons, various efforts have been made to identify and/or compensate for the effects of artifact presence in the signal received for analysis. In the instance of the aforementioned Link patents, several successive blood pressure pulses are continually averaged to minimize the effect of an artifact. It will be appreciated that in some instances such modification of data may have little or no effect on the accurate determination of blood pressure values. However in other instances this modification of data may, depending upon its time of occurrence and the particular algorithm used in the analysis, seriously distort the resulting blood pressure determination.

Accordingly it is a principle object of the invention to provide an apparatus and a method for producing information indicative, with increased accuracy, of the physical condition of the living test subject. Included within this object is the provision of a method and apparatus for accurately determining blood pressure.

It is a further object of the invention to provide an improved method and apparatus for measuring blood pressure, which improved method and apparatus is less prone to erroneous blood pressure determinations as a result of artifacts appearing in the sensed signal representative of pressure pulsations within the blood vessel.

SUMMARY OF THE INVENTION

The apparatus and the method of the invention are founded on the premise that by deleting all information during a particular time frame in which an artifact has been recognized, the valid information otherwise appearing during the time frame may have been critical to the accurate determination of some physical condition of the patient, as for instance, diastolic or systolic pressure. In order to avoid the loss of such information, the invention provides an apparatus and method for recognizing the occurrence of an artifact in the sensed pressure signals and utilizes such recognition to control the reacquisition of pulse pressure data during the same conditions of applied cuff pressure as existed at the time the artifact was detected. Briefly, this is accomplished by repeating the applied pressure at which the artifact occurred and taking new pulse pressure data at that time. Means are employed to inhibit the processing of artifact data by the signal analysis circuitry and to accept new data in place thereof. In this manner, the data utilized by the decision making circuitry is, or has a greater probability of being, accurately representative of the blood pressure conditions within the blood vessel.

The invention comprises an apparatus for producing information indicative of the physical condition of a living test subject comprising means for applying a selectively changeable pressure to the test subject adjacent a blood vessel; means for measuring a time dependent fluctuating value representative of pulsatile pressure within the blood vessel; means for measuring a value representative of the selectively changeable pressure applied externally adjacent the blood vessel; signal processing means responsive in a predetermined manner to the pulsatile pressure value as a function of the applied pressure for providing an output indication of the physical condition of the living test subject; means for detecting an artifact value in at least the pulsatile pressure representing value and providing a control indication thereof; means responsive to an artifact indication for inhibiting response of the signal processing means to the detected artifact value; and control means associated with the pressure applying means for repeating the applied pressure at which the indication of an artifact occurred in response to an artifact indication, thereby to seek artifact-free values of the pressures.

In a preferred embodiment the control means for repeating the applied pressure comprise means for initially adjusting the applied pressure substantially to a pressure previously attained and which is other than the pressure at which the artifact occurred and for subsequently changing the adjusted applied pressure at least to the pressure at which the respective artifact had previously occurred.

In one embodiment, the signal processing means is inhibited from receiving and/or further processing pressure signals until and only until the pressure at which the artifact occurred is re-attained.

In another embodiment, the signal processing means is inhibited substantially only until the adjusted pressure is attained, and the values of the applied and the pulsatile pressures received by the signal processing means during the repetition of applied pressures replace the pressure values received during the corresponding previously applied pressures.

In another embodiment of the invention the detected artifact indications are counted and means are provided for disabling at least the applied pressure repeating means when the artifact count reaches some predetermined value, thereby limiting the maximum time required to obtain an output indication of the patient's physical condition. The response-inhibiting means to the signal analyzing means may also be disabled following this count.

In a still further embodiment of the invention, the selectively changeable applied pressure is increased, as for instance linearly, prior to each successive pressure pulsation, the means for repeating the applied pressure is responsive automatically to the artifact indication, and the applied pressure is of course adjusted downwardly but not necessarily to zero, to begin its repeat run through the pressure at which the artifact occurred.

The method and apparatus of the invention finds particular utility in the measurement of diastolic and systolic blood pressures and wherein the pressure applying means comprises the blood pressure cuff and the means for measuring both the pulsating pressure and the applied pressure comprises a pressure transducer in communication with the cuff.

The invention further resides in an improved method for producing information indicative of at least one of the diastolic and systolic pressures in the blood vessel of a living test subject including applying a selectively changeable pressure to the test subject adjacent the blood vessel; measuring for a time dependent fluctuating value representative of pulsatile pressure within the blood vessel, measuring for value representative of a selectively changeable pressure applied externally adjacent the blood vessel, and analyzing the pulsatile pressure value in a predetermined manner as a function of the applied pressure to provide an output indication of at least one of the diastolic and systolic pressures in the subject blood vessel, and wherein the improvement comprises detecting an artifact value in at least the pulsatile pressure representing value and providing a control indication thereof; inhibiting the analysis of the pulsatile pressure as a function of the applied pressure in response to the artifact indication thereby to at least reject the detected artifact value; and controlling the applied pressure in response to an indication of artifact occurrence such that the applied pressure at which the artifact occurred is repeated.

In a preferred embodiment of the invention the improved method automatically repeats the applied pressure at which the artifact indication occurs by initially adjusting the applied pressure substantially to a pressure previously attained and other than the pressure at which the artifact occurred, and subsequently changing the adjusted applied pressure at least to the pressure at which the respective artifact previously occurred.

In yet another preferred embodiment the improved method includes the steps of counting the artifact indications, and preventing at least the repetition of the applied pressure in response to subsequent artifact values when a predetermined count of artifact indication is exceeded, thereby to limit the maximum time required to obtain an output indication of blood pressure.

BRIEF DESCRIPTION OF THE DRAWINGS

FIG. 4 is a plot of cuff pressure versus time similar to FIG. 2;

FIGS. 5a and 5b illustrate the pressure signals received by the signal processing circuitry during intervals A and B of FIG. 4 respectively in accordance with an alternate embodiment of the invention;

DETAILED DESCRIPTION OF THE PREFERRED EMBODIMENT

Figure 1:
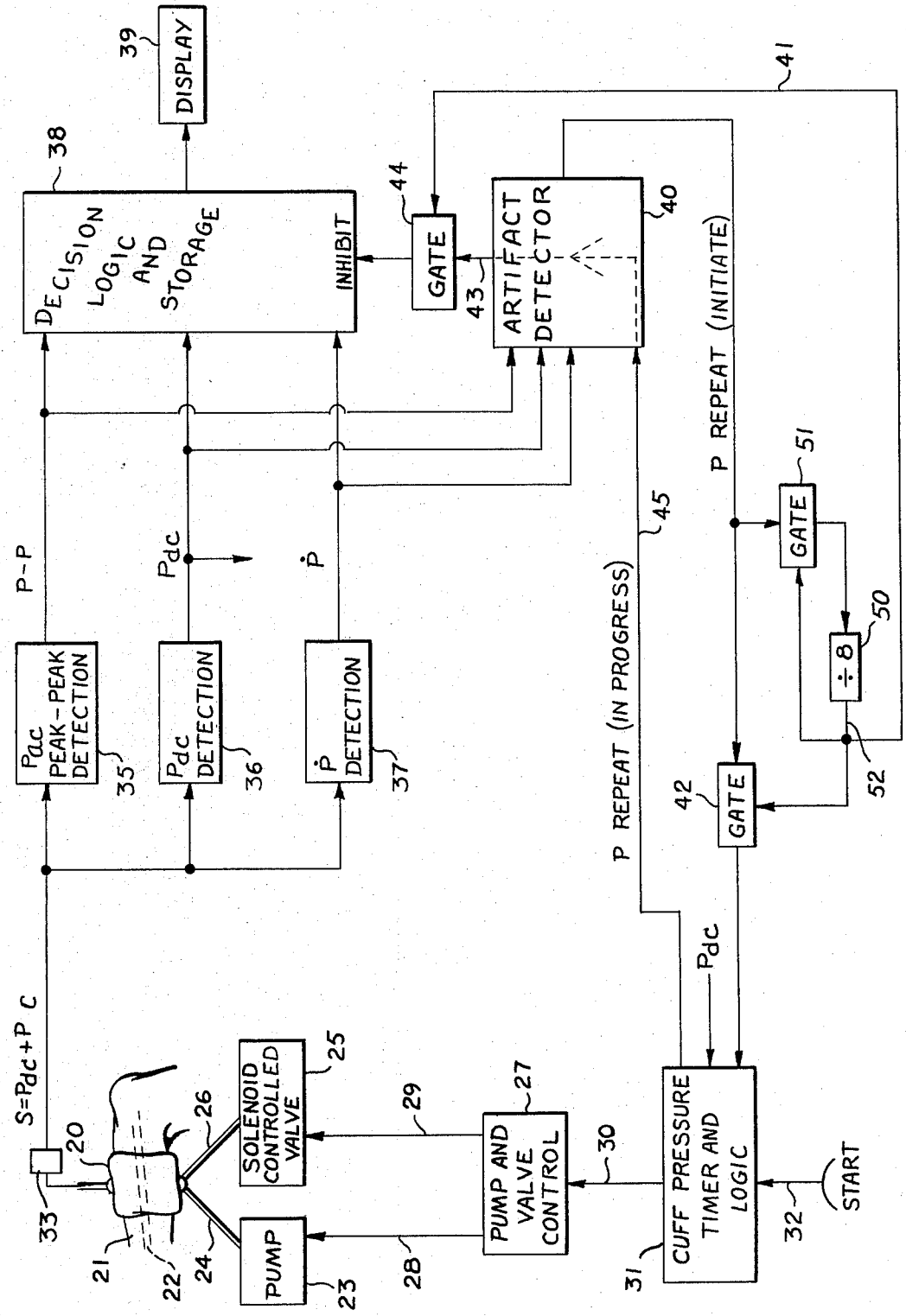
FIG. 1 is a block diagram illustrating the apparatus and process of the present invention in combination with blood pressure measuring equipment.
Figure 2:
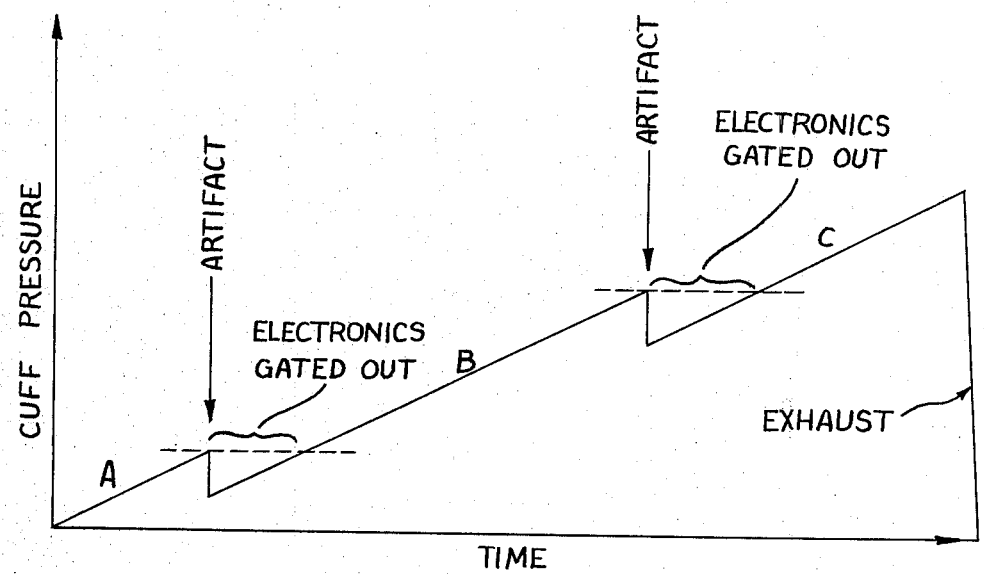
FIG. 2 illustrates a plot of the applied cuff pressure versus time illustrating the technique of the invention.

Referring now to the figures, and in particular FIG. 1, the preferred embodiments of the invention can be better understood. Means for applying a differable or changeable pressure adjacent a blood vessel, said pressure applying means comprising a blood pressure measuring means in particular a cuff 20, is shown in position about an arm 21 containing an artery 22 therein. The cuff 20 can be a typical blood pressure cuff such as those utilized when one is making use of a stethoscope to hear Korotkoff sounds. Also a part of said pressure applying means along with the cuff is the pump or pressurizing device 23 acting through the tubing 24. A solenoid controlled valve 25 acting through tubing 26 may be controlled to exhaust air pressure from the cuff 20.

In the illustrated embodiment, pump 23 and valve 25 are controlled by a pump and valve control unit 27 via lines 28 and 29 respectively, the control unit 27 in turn being automatically controlled via line 30 by the cuff pressure timer and logic circuitry 31. The normal control of pump 23 and valve 25 is initiated by a start signal applied on line 32 to an input of timer and logic circuitry 31.

In the illustrated embodiment of the invention the timer and logic circuitry 31 controls pump 23 and valve 25 respectively such that the cuff 20 applies a linearly increasing pressure to the arm 21 at a predetermined rate over the pressure range of interest and the valve rapidly bleeds or dumps air pressure at the completion of that range. Typically the applied pressure ramp rate will be somewhere in the range of 2 mm–15 mm per second, this also being approximately the change in applied pressure between successive blood pressure pulses where the patients heart rate is about 60 beats per minute. In the illustrated embodiment the pressure ramp rate is about 5–7 mm per second. However, the logic of circuitry 31 is capable, as will be hereinafter described, of controlling pump 23 and valve 25 such that the normally continuous increase in pressure applied by cuff 20 may be interrupted and temporarily reduced or at least maintained at a particular pressure for the subsequent acquisition of data at those pressure levels.

In another embodiment of the invention the cuff is pumped initially and quickly to a pressure greater than any likely systolic pressure and then allowed to slowly reduce toward zero pressure by a controlled air leak and in an approximately linear fashion. The pressure resulting in the cuff 20 is the sum of the differable pressure applied by the pump 23 and a pulsating pressure due to the time-dependent pulsatile pressure surges within the artery 22, this sum being represented as S in FIG. 1. The cuff pressure is measured by the pressure transducer 33 or by other convenient means. Although the signal S from transducer 33 comprises a sum of the applied pressure and the pulsatile pressure, it should be noted that the applied pressure (designated $P_{dc}$) is many times greater than the pulsatile pressure (designated $P_{ac}$) and accordingly, the value of S is substantially equal to the pressure applied by cuff 20.

The output S of pressure transducer 33 is extended to signal processing circuitry which responds in a predetermined manner in accordance with a particular algorithm to ascertain and display both diastolic and systolic blood pressure values for the patient being monitored.

Typically, the signal S from transducer 33 is extended to circuits 35, 36 and 37 which are of a nature to determine, respectively, the peak-to-peak (P—P) magnitude of each succeeding pulse in the pulsatile pressure $P_{ac}$; the so called DC or applied pressure level, $P_{dc}$; and the first time derivative ($\dot{P}$) of the $P_{ac}$ pulsatile pressure. For all intents and purposes, the output of $P_{dc}$ detection circuit 36 has the magnitude of the input S signal with the very small $P_{ac}$ pulsatile pressure component removed therefrom. The $P_{ac}$ peak-to-peak detection circuit 35 includes peak-to-peak detection circuitry for providing output signals P—P representative of the peak-to-peak values of the respective blood pressure pulses. The $\dot{P}$ detection circuitry 37 comprises a differentiator for obtaining the first time derivative of the $P_{ac}$ component of the S input signal. The circuits for obtaining the aforementioned values are described in the aforementioned U.S. patents to Link and Link et al, wherein it is further indicated that the peak-to-peak (P—P or $P_{ac}$) value is utilized in making systolic pressure measurements, the first time derivative ($\dot{P}$) value is used in making diastolic pressure measurements and the S or $P_{dc}$ value denotes the applied pressure for respective samples of P—P and $\dot{P}$.

At this juncture it is appropriate to note that analog and/or digital circuitry may be employed for circuits 35, 36 and 37 and many or all of the remaining functions to be discussed may be implemented by analog or digital circuitry, with commercially available microprocessors and other digital circuitry being preferred. Implicit in this discussion will be the inclusion of appropriate analog to digital converters and the use of a program suited for directing the requisite decision and control functions of a microprocessor which program in view of the accompanying disclosure is within the skill of one ordinarily skilled in the art.

Suitable decision logic 38 is responsive to the P—P, the $P_{dc}$ and $\dot{P}$ signals of detection circuits 35, 36 and 37 respectively to determine, and display via display means 39, the diastolic and systolic blood pressures of the patient in accordance with the teachings contained in the aforementioned U.S. patents to Link and Link et al.

Included within the block 38 of FIG. 1 entitled "Decision Logic and Storage" there may be included data storage means for temporarily storing P—P, $P_{dc}$ and $\dot{P}$ data, particularly if a particular logic decision may be made only some extended time after the acquisition of the particular data in question. An example of this would exist in a system employing a down-ramp rather than up-ramp of applied pressure because the systolic pressure is recognized as being that applied pressure at which the P—P value is substantially one half its maximum value and being an applied pressure greater than that at which maximum P—P occurs.

The decision logic and/or storage circuitry 38 is provided with logic means, generally designated "INHIBIT", for inhibiting or blocking the further acquisition of P—P, $P_{dc}$ and $\dot{P}$ data from the transducer 33 for a reason to be hereinafter explained. Alternately, the circuitry for providing this "INHIBIT" function might be located intermediate the transducer 33 and the inputs to the respective detection circuits 35, 36 and 37, with provision being made to extend the S signal (for $P_{dc}$) to cuff control circuitry 31.

Artifact detection circuitry 40 receives inputs P—P, $P_{dc}$ and $\dot{P}$ from the outputs of detection circuits 35, 36 and 37 respectively. The artifact detector 40 suitably structured to recognize and provide an indication of the occurrence of an artifact in any or all of its input signals. The circuitry or microprocesser program for detector 40 may be structured to employ only one criterion in its search for artifact or a variety of different criteria. For example, known circuitry may be provided to initiate the repetition of the applied pressure in cuff 20 at which the particular artifact was detected. The signal on line 41 is extended, via normally open gate 42, to an input of the timer and logic circuitry 31 which controls the pressure applied by cuff 20. The applied pressure, either as represented by signal S or preferably by $P_{dc}$ at the output of circuit 36, is also extended to an input of timer and logic circuitry 31 for the initial purpose of storing the $P_{dc}$ value at which the artifact occurred and for the subsequent purpose of recognizing when that stored value of applied pressure has been reached during the repetition run to be hereinafter described.

In addition to the artifact indication control signal appearing on line 41, the detector 40 additionally provides a similar control signal on line 43 initiated by the artifact indication and of usually longer duration which is selectively extended through normally open gate 44 to the INHIBIT circuitry associated with the decision logic and storage 38. Control signal 43 is operative to prevent the processing of the artifact value as a valid data point, either by providing for subsequent and presumably better data to be written over stored artifact data or preferably, by preventing the effective entry of the artifact into storage in circuit 38 in the first place, as with a gate. If for instance the storage provided in unit 38 comprises a push-down stack, a recirculating memory or a random access memory (RAM), the signal 43 may control the address positions in the memory such that invalid data may be omitted and/or written over by new data. In either event, the effect of signal 43 is to eliminate the detected artifact value from the data stream to be subsequently processed by the decision logic 38.

The duration of signal 43 for the purpose of inhibiting the entry of new data into the logic and storage circuitry 38 is determined by the duration of the dotted extension of line 45 which represents that the repetition of some portion of the range of applied pressure is in progress. The signal on line 45 is provided by cuff pressure timer and logic 31 as will hereinafter be described and serves, for instance, to reset a bistable circuit (not shown) associated with detector 40 which was set by the recognition of an artifact indicated by signal 41.

Suitable timer and logic circuitry 31 for controlling the pressure applied by cuff 20 operate in one embodiment in the manner illustrated in FIGS. 2 and 3a–e. Referring to those Figures, it will be noted in FIG. 2 that the applied pressure of cuff 20 increases linearly in several segments A, B and C respectively. The cuff pressure represented at the origin of the plot may be about 40 mm Hg, below which no meaningful measurements are taken. As the cuff pressure increases in segment A, pressure data points occur at each successive pulse, or about once each second. These pressure data points may be $P_{dc}$ and/or P—P and/or $\dot{P}$, with P—P being illustrated in FIGS. 3a–e.

Figure 3A:
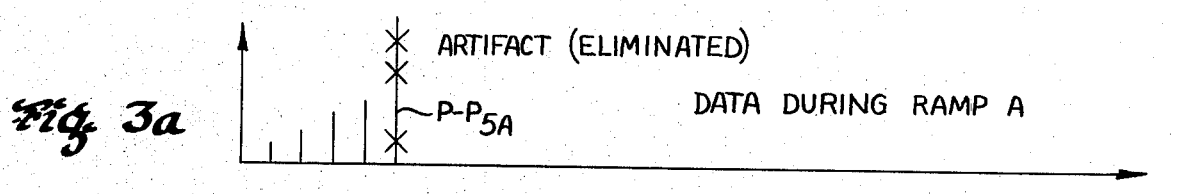
FIGS. 3a, 3b and 3c illustrate the pressure signals seen by the signal processing circuitry during intervals A,B and C respectively of the cuff pressure illustrated in FIG. 2.
Figure 3B:
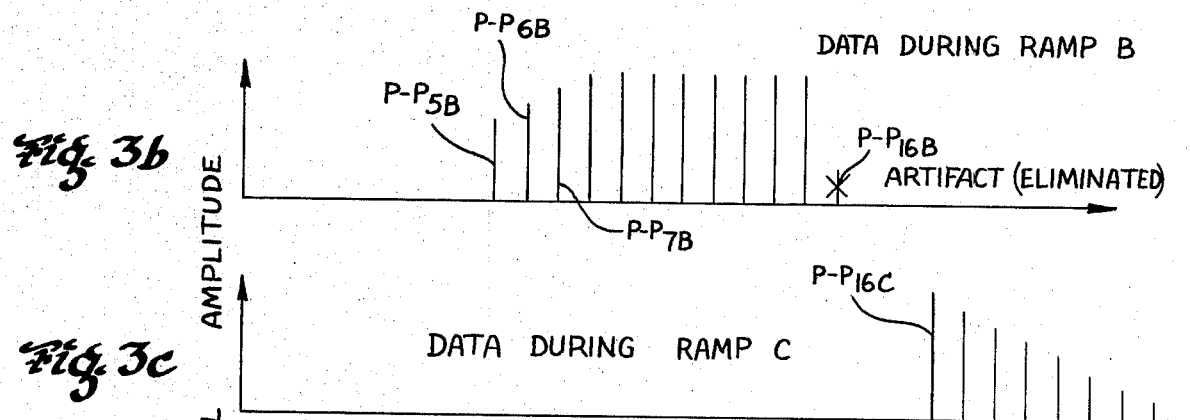

In FIG. 3a, when the fifth apparent P—P value P—$P_{5a}$ is sensed at an applied pressure of 60 or 70 mm Hg, it is recognized by detector 40 to be an artifact due to its excessive amplitude. This recognition acts, via line 41, to direct the logic of circuitry 31 to provide a control signal, via line 29, to valve 25 to quickly drop the cuff pressure by a predetermined amount, for instance 15–20 mm Hg. Then the logic and timer 31 return control to the pump 23 for resuming the linear upward pressure ramp at the same rate as previously, but from the new downwardly adjusted pressure level. This resumed ramp is designated B. The operation of dropping the pressure and then resuming the upward ramp serves to repeat the applied pressure at which the artifact was detected in order that presumably accurate pressure data may be taken substantially thereat, as represented by the valid P—P value P—$P_{5b}$ in FIG. 3b. Continuation of ramp B results in additional valid P—P values P—$P_{6b}$, P—$P_{7b}$ etc.

In this embodiment, it has been predetermined that the pressure data points accepted during segment A (i.e. P—$P_{a1}$-P—$P_{a4}$) should be retained for analysis. Therefore, a "P REPEAT" signal is provided by circuitry 31 on line 45 for inhibiting the input of data to circuitry 38 until the cuff pressure, as indicated by $P_{dc}$, returns to the level at which the artifact was sensed, whereupon the new sample (P—$P_{5b}$) is taken at the next heart beat.

Figure 3C:
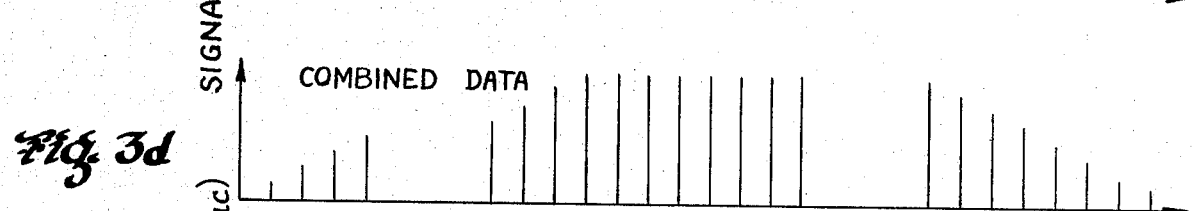

It will be noted that another artifact appears at the apparent P—$P_{16b}$ value in ramp segment B, whereupon the aforementioned operation is repeated to obtain the valid P—$P_{16c}$ value of FIG. 3c.

Figure 3D:
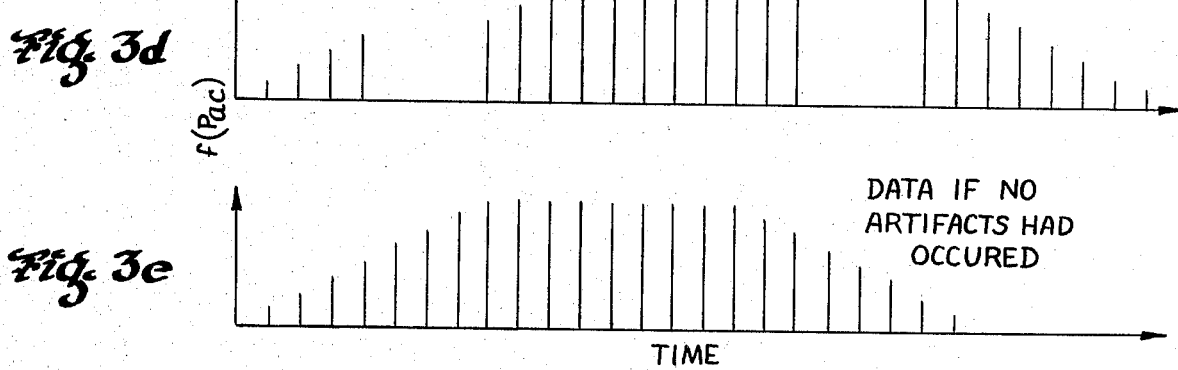
FIG. 3d is a composite of FIGS. 3a, 3b and 3c.
Figure 3E:
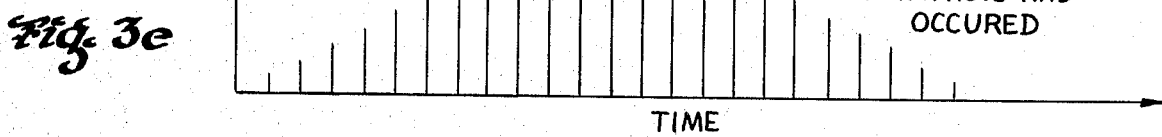
FIG. 3e is an illustration of the ideal situation in which no artifacts occurred in the pressure signals provided to the signal analysis circuitry.

Referring to FIG. 3e, there is illustrated a normal pattern of P—P data points when no artifacts are detected. The FIG. 3d illustrates the data points taken in accordance with the invention when two artifacts were present. It will be noted that this latter run, while necessarily longer than that of FIG. 3e, does contain the same number and values of pressure data points, and thus provides the same data to circuitry 38 for analysis.

Instead of the operation of logic 31 illustrated in FIGS. 2 and 3a–e, the logic might be configured to provide the operation illustrated in FIGS. 4, 5a and 5b. Here the cuff pressure ramp is identical to that of FIG. 2, however, the P REPEAT signal on line 45 is present only long enough for signal 43 to eliminate the artifact represented by the apparent P—$P_{5a}$ value, but not long enough to block the acceptance of new P—$P_{3b}$ and P—$P_{4b}$ values which are written into memory over (cancelling) the old values P—$P_{3a}$ and P—$P_{4a}$. In this way, segment B includes not only the new pressure values beginning with the repetition of the cuff pressure at which the artifact occurred, but also new pressure values throughout the repeated portion of the applied pressure. It will be appreciated that the "end-to-end" data patch might be made at any point within the repeated portion of the applied cuff pressure.

Figure 6:
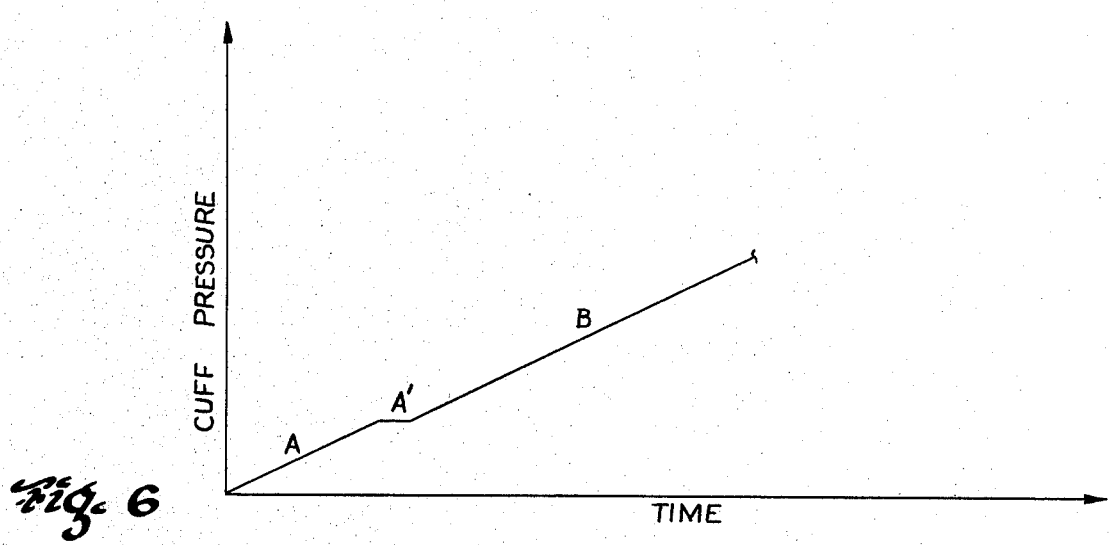
FIG. 6 is a plot of the applied cuff pressure versus time in accordance with a still further embodiment of the invention.
Figure 7A:
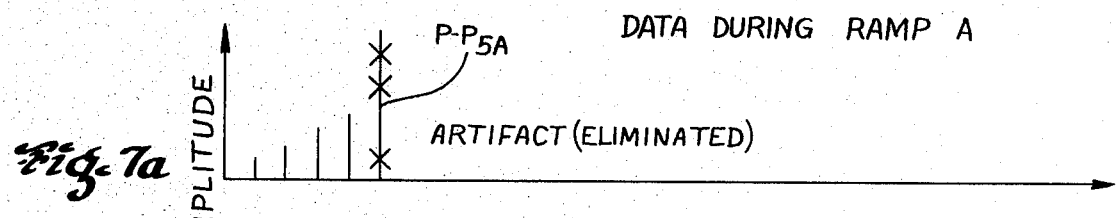
FIGS. 7a, 7b and 7c illustrate the pressure signals applied to the signal processing circuitry during intervals A, A' and B respectively of FIG. 6.
Figure 7B:
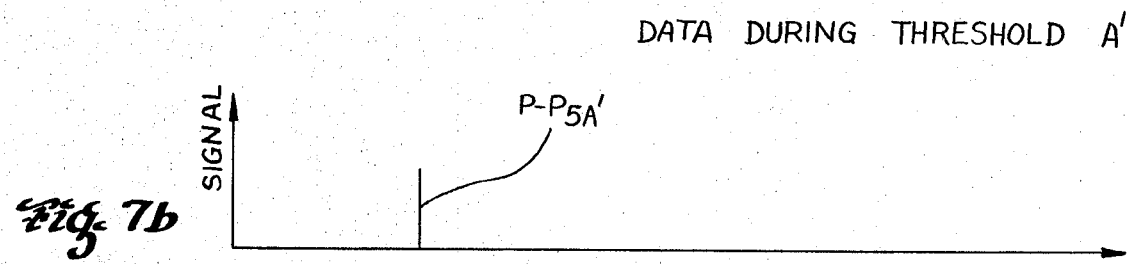
Figure 7C:
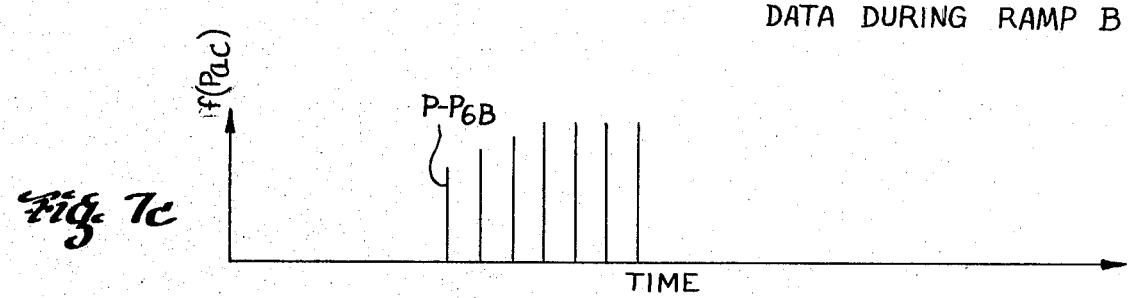

The FIGS. 6 and 7a–c illustrate still another mode of operation in which the timer and logic circuitry 31 is configured or programmed such that the repetition of the applied cuff pressure at which the artifact occurred does not require a dropping of the pressure and the attendant repetition of other intermediate cuff pressures. Instead, as illustrated in FIG. 6, the cuff pressure is maintained constant at the pressure at which the artifact occurred until the next heart beat has occurred. This results in the brief segment A' in FIG. 6 and the attendant P—$P_{5a}'$ value in FIG. 7b. The ramp is then resumed to provide segment B which first records the valid P—P 6b value of FIG. 7c. As in the arrangement of FIGS. 4, 5a and 5b, the signal on line 45 is present only long enough to effect elimination of the artifact represented by the apparent P—$P_{5a}$ value.

It is appropriate to note that although the invention has been described in conjunction with a continuous, linear, up-ramped cuff pressure the principle would be equally applicable to stepped cuff pressure and/or decreasing or down-ramped pressures, though in the latter case the pressure would be adjusted upwardly for a detected artifact and would repeat a portion of the declining pressure.

Returning to FIG. 1, there is illustrated a counter 50 which divides by eight or some other predetermined appropriate number for the purpose of limiting the number of times the system may repeat an applied pressure as a result of the detection of an artifact. Through a comparison of FIGS. 3d and 3e it is evident that the blood pressure measuring run might otherwise be greatly extended in time if a large number of artifacts are present. Typically, each detected artifact might extend the run time by 2-5 seconds depending on which of the aforementioned techniques is employed. Thus, by extending the artifact indication signal 41 through gate 51 to the trigger input of ÷8 counter 50, the counter will provide an output control signal on line 52 when eight successive artifacts have been detected. The gate 51 is controlled by the output 52 of counter 50 and blocks further input of trigger signals 41 to the counter when it reaches a count of eight.

The signal on line 52 from counter 50 is extended to the control inputs of gates 42 and 44 for the purpose of closing the gates and preventing the repetition of cuff pressure and deletion of artifact values after eight artifacts have been detected in order to prevent the inordinate extension of the run time. In such instance, further data points containing artifacts might be accepted and averaged for subsequent analysis by circuit 38. Alternately, the artifact indication signal 41 might be utilized (not shown) to enter standardized or averaged pressure values in circuit 38 when the counter 50 closes gate 44.

It will be appreciated that in the embodiments described, as well as in other blood pressure measuring arrangements containing artifact detectors but with no provision for repetition of the cuff pressure, an artifact counter may act to respond to some predetermined number of detected artifacts (ie. 5-10) to terminate the entire measurement run and display an abort or error indication. This would prevent grossly inaccurate blood pressure measurements when the patient is in a condition which produces a large number of artifacts.

The invention may be embodied in other specific forms without departing from the spirit or essential characteristics thereof. It will be thus appreciated that instead of the discrete circuitry as illustrated by the block diagrams in FIG. 1, the same result may be achieved by logical operations on stored data under the command of a pre-programmed microprocessor. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. Apparatus for producing information indicative of the diastolic and systolic pressures of a living test subject comprising:
    means for controllably applying a selectively changeable pressure to the test subject adjacent a blood vessel;
    means for measuring a time dependent fluctuating value representative of pulsatile pressure within the blood vessel;
    means for measuring a value representative of the selectively changeable pressure applied externally adjacent the blood vessel;
    signal producing means responsive in a predetermined manner to said pulsatile pressure representing value as a function of the applied pressure for providing an output indication of the diastolic and systolic pressures of the living test subject;
    means for detecting an artifact value in at least said pulsatile pressure representing value across at least the diastolic-systolic pressure range of said test subject and providing a control indication thereof;
    means responsive to a said artifact indication for inhibiting said response in said predetermined manner of said signal processing means to said detected artifact value;
    control means associated with said pressure applying means for normally changing said applied pressure in a single direction across at least the diastolic-systolic pressure range of said test subject and for automatically repeating the applied pressure at which an indication of an artifact occurred through a predetermined range within and normally less than the pressure range previously applied in response to each said artifact indication across at least the diastolic-systolic pressure range of said test subject, thereby to seek artifact-free values of said pressures.

2. The apparatus of claim 1 wherein said control means for repeating the applied pressure comprises means for initially adjusting the applied pressure substantially to a pressure previously attained and other than the pressure at which said artifact occurred and for subsequently changing the adjusted applied pressure at least to said pressure at which the respective said artifact previously occurred.

3. The apparatus of claim 2 wherein said signal processing means is inhibited from responding to said detected artifact signal by inhibiting response to said pulsatile and said applied pressure values only until said pressure at which said artifact occurred is re-attained.

4. The apparatus of claim 2 wherein said signal processing means is inhibited from responding to said detected artifact signal by inhibiting response to said pulsatile and said applied pressure values substantially only until said adjusted pressure is attained, and the values of said applied and said pulsatile pressures received by said signal processing means during said repetition of the applied pressure replace said pressure values received during the corresponding previously applied pressure.

5. The apparatus of claim 2 including means responsive to a predetermined number of detected artifact indications for disabling at least said applied pressure repeating means from responding to subsequent artifact values, thereby to limit the maximum time required to obtain an output indication of physical condition.

6. The apparatus of claim 2 wherein the pressure applying means comprises a blood pressure cuff, the means for measuring both the pulsating pressure and the applied pressure comprises a pressure transducer in communication with the cuff, and said signal processing means responds to said pulsatile pressure and said applied pressure to provide output indications of the diastolic and systolic pressures of the subject's blood vessel.

7. The apparatus of claim 1 wherein said selectively changeable applied pressure is normally changed prior to each successive pulsation of pressure within the subject's blood vessel.

8. The apparatus of claim 7 wherein said normal change in applied pressure prior to each successive pressure pulsation comprises an increase, and said applied pressure is decreased by a predetermined value to comprise said repeat adjustment thereto.

9. In a method for producing information indicative of the diastolic and systolic pressure in the blood vessel of a living test subject, including applying a selectively changeable pressure to the test subject adjacent the blood vessel, measuring for a time dependent fluctuating value representative of pulsatile pressure within the blood vessel, measuring for a value representative of a selectively changeable pressure applied externally adjacent the blood vessel, and analyzing the pulsatile pressure representing value in a predetermined manner as a function of the applied pressure to provide an output indication of the diastolic and systolic pressures in the subject's blood vessel, the improvement comprising:

detecting an artifact value in at least the pulsatile pressure representing value across at least the diastolic-systolic pressure range of said test subject and providing a control indication thereof;

inhibiting said analysis of said pulsatile pressure in said predetermined manner as a function of the applied pressure in response to the artifact indication thereby to at least reject the detected artifact value; and controlling the applied pressure to normally change in a single direction across at least the diastolic-systolic pressure range of said test subject and in response to an indication of artifact occurrence to automatically repeat the applied pressure at which the artifact occurred through a predetermined range within and normally less than the pressure range previously applied.

10. The method of claim 9 wherein controlling the applied pressure to repeat the applied pressure at which the artifact indication occurred comprises initially adjusting the applied pressure substantially to a pressure previously attained and other than the pressure at which said artifact occurred, and subsequently changing the adjusted applied pressure at least to said pressure at which the respective said artifact previously occurred.

11. The method of claim 10 wherein the inhibition of the analysis of the pulsatile pressure continues only until the applied pressure which said artifact occurred is re-attained.

12. The method of claim 10 wherein the inhibiting of the analysis of the pulsatile pressure continues only until the adjusted pressure is attained, and including the step of analyzing the applied and the pulsatile pressure values occurring during said change in and repetition of the applied pressure to to exclusion of said pressure values analyzed during the corresponding previously applied pressure.

13. The method of claim 10 including the steps of counting the artifact indications, and preventing at least said repetition of the applied pressure in response to subsequent artifact values when a predetermined count of artifact indications is exceeded, thereby to limit the maximum time required to obtain an output indication of blood pressure.

14. The method of claim 10 including normally changing the applied pressure prior to each successive pulsation of pressure within the subjects blood vessel.

* * * * *